United States Patent [19]

Cheng

[11] Patent Number: 5,128,491
[45] Date of Patent: Jul. 7, 1992

[54] PROCESS FOR THE PREPARATION OF GLYCIDYL ETHERS OF DI-SECONDARY ALCOHOLS WITH HIGH MONOMER CONTENT

[75] Inventor: Chi-Wen F. Cheng, New City, N.Y.

[73] Assignee: Ciba-Geigy Corporation, Ardsley, N.Y.

[21] Appl. No.: 738,072

[22] Filed: Jul. 30, 1991

[51] Int. Cl.$^5$ .......................................... C07D 301/28
[52] U.S. Cl. .................................................... 549/516
[58] Field of Search ......................................... 549/516

[56] References Cited

U.S. PATENT DOCUMENTS

| | | | |
|---|---|---|---|
| 3,096,349 | 7/1963 | Meyer et al. | 549/516 |
| 3,129,232 | 4/1964 | Terford et al. | 549/516 |
| 4,284,574 | 8/1981 | Baggs | 549/556 |
| 4,810,808 | 3/1989 | Tomita et al. | 549/516 |

FOREIGN PATENT DOCUMENTS 121260 10/1984 European Pat. Off. ............ 549/516

Primary Examiner—J. E. Evans
Attorney, Agent, or Firm—JoAnn Villamizar

[57] ABSTRACT

The present invention relates to a process for the preparation of a glycidyl ether of a di-secondary alcohol with a monomer content of about 80% to about 90% of the formula (I)

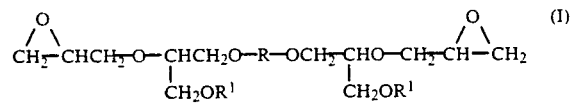

comprising the steps of:

(a) reacting a di-secondary alcohol of the formula (II)

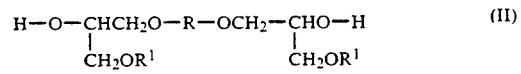

with epichlorohydrin in the presence of an alkali and a phase transfer catalyst to produce a glycidyl ether with a monomer content of about 60% to about 75%; and (b) reacting said glycidyl ether with a monomer content of about 60% to about 75% with epichlorohydrin in the presence of an alkali and benzyltrimethylammonium chloride to produce a glycidyl ether of a di-secondary alcohol with a monomer content of about 80% to about 90%.

20 Claims, No Drawings

PROCESS FOR THE PREPARATION OF GLYCIDYL ETHERS OF DI-SECONDARY ALCOHOLS WITH HIGH MONOMER CONTENT

BACKGROUND OF THE INVENTION

A process for making diglycidyl ethers of di-secondary alcohols from di-secondary alcohols and epichlorohydrin in the presence of an alkali and a phase transfer catalyst is disclosed in U.S. Pat. No. 4,284,574. The diglycidyl ethers produced in accordance with the teachings therein have a monomer content of about 60% to about 75%. Diglycidyl ethers with monomer contents of about 80% to about 90% are desirable because higher epoxy functionality will lead to higher crosslinking density of cured thermosets which have better thermal properties (e.g. higher glass transition temperature, higher decomposition temperature) and better solvent resistance.

Accordingly, it is an object of the present invention to provide a process for the preparation of diglycidyl ethers of di-secondary alcohols with a monomer content of about 80% to about 90%.

It is a further object of the present invention to provide a process for the preparation of diglycidyl ethers of di-secondary alcohols with less monohydroxyl impurities than the prior art process.

Various other objects and advantages of this invention will become apparent from the following description thereof.

SUMMARY OF THE INVENTION

The present invention relates to a process for the preparation of a glycidyl ether of a di-secondary alcohol with a monomer content of about 80% to about 90% comprising:

(a) reacting a di-secondary alcohol with epichlorohydrin in the presence of an alkali and a phase transfer catalyst to produce a glycidyl ether with a monomer content of about 60% to about 75%; and (b) reacting said glycidyl ether with a monomer content of about 60% to about 75% with epichlorohydrin in the presence of an alkali and benzyltrimethylammonium chloride to produce a glycidyl ether of a di-secondary alcohol with a monomer content of about 80% to about 90%.

DETAILED DESCRIPTION OF THE INVENTION

The present invention relates to a process for the preparation of a glycidyl ether of a di-secondary alcohol with a monomer content of about 80% to about 90% of the formula (I)

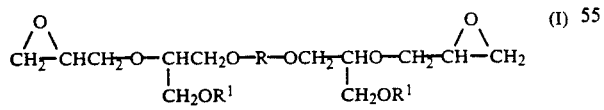

where R represents (i) a phenylene or naphthylene group or (ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms, each phenylene group or each naphthylene group optionally being substituted in the ring or rings by one or two alkyl groups, each of from 1 to 4 carbon atoms, or by one or two chlorine or bromine atoms, and each $R^1$ represents (iii) a straight chain or branched alkyl groups of 1 to 16 carbon atoms, which may be substituted by one to four chlorine or bromine atoms, or (iv) a straight chain or branched alkenyl group of 2 to 6 carbon atoms, which may be substituted by one to four chlorine or bromine atoms, or (v) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or (vi) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or (vii) a mononuclear cycloalkyl group of 3 to 6 carbon atoms, or (viii) a mononuclear cycloalkylalkyl group of from 4 to 10 carbon atoms comprising the steps of:

(a) reacting a di-secondary alcohol of the formula (II)

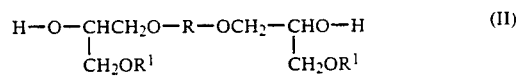

wherein R and $R^1$ are defined hereinabove, with epichlorohydrin in the presence of an alkali and a phase transfer catalyst to produce a glycidyl ether with a monomer content of about 60% to about 75%; and (b) reacting said glycidyl ether with a monomer content of about 60% to about 75% with epichlorohydrin in the presence of an alkali and benzyltrimethylammonium chloride to produce a glycidyl ether of a di-secondary alcohol with a monomer content of about 80% to about 90%.

Preferably, the groups $R^1$ are the same and each represents an alkyl group of 1 to 14 carbon atoms, an allyl group, a cyclohexyl group, or a benzyl group are employed. Particularly preferred are alcohols wherein $R^1$ is an alkyl group of 1 to 14 carbon atoms.

Further preferred compounds produced in accordance with the present invention are those wherein R is an m- or p-phenylene group or a radical consisting of two phenylene rings linked in the o-o', o-p', or p-p' position by an alkylene group of 1 to 4 carbon atoms. Especially preferred diglycidyl ethers of a dihydric phenol are those wherein R represents a group of the formula

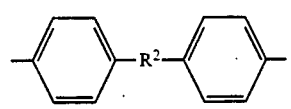

where $R^2$ represents a methylene or isopropylidene group, and those where each $R^1$ represents an alkyl group of from 1 to 12 carbon atoms, more particularly of from 1 to 6 carbon atoms.

The di-secondary alcohols of formula (II) are, in general, known compounds (see, e.g. West German Offenlegungsschrift No. 2,838,841) and may be prepared by any of the following routes:

(i) Reaction between 1.5 to 2.5, and preferably about 1.8 to 2.2, moles of a monoglycidyl ether of the formula (III)

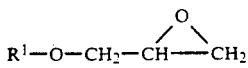 (III)

and one mol of a dihydric phenol of the formula (IV)

HO—R—OH     (IV)

where R and $R^1$ are as hereinbefore defined.

The reaction may be affected in the presence of a basic catalyst, such as a tertiary amine, a quaternary ammonium base, an alkali metal hydroxide, or a quaternary ammonium salt, such as benzyltrimethylammonium chloride, usually by heating the reactants at 80° to 180° C. without a solvent.

(ii) Reaction between at least two moles of an alcohol of the formula (V)

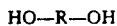 (V)

with one mole of a diglycidyl ether of a dihydric phenol of the formula (VI)

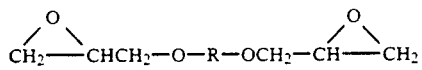 (VI)

where R and $R^1$ are as hereinabove defined.

This reaction may be affected in the presence of a basic catalyst, such as a tertiary amine, a quaternary ammonium base, an alkali metal hydroxide, or a quaternary ammonium salt, usually by heating the reactants at a temperature in the range 80° to 180° C. without a solvent. Alternatively, this reaction may be carried out in the presence of a Lewis acid catalyst, such as a boron trifluoride complex or stannic chloride. When the reaction is carried out in this way, an excess of the alcohol of formula XV is usually employed and the reaction is carried out at a temperature between 50° C. and 100° C.

The excess of the alcohol is then removed by distillation prior to glycidylation.

(iii) Reaction between one mole of an alkali metal salt of a dihydric phenol of formula (VI) either prepared separately or in situ, with about two mols of a chlorohydrin of formula (VII)

 (VII)

where $R^1$ is as hereinbefore defined.

The reactants are usually heated at a temperature of between 50° and 150° C., preferably without an added solvent.

The di-secondary alcohol is reacted with epichlorohydrin in the presence of an alkali and a phase transfer catalyst to produce a glycidyl ether with a monomer content of about 60 to about 75%.

Preferably, the di-secondary alcohol of formula (II) is reacted with at least about 2.5, and preferably 3 to 8, molar equivalents of epichlorohydrin in the presence of about 1.5 to about 2.5 moles, preferably about 1.8 to about 2.2 moles, most preferably 2.0 moles of an alkali and in the prece of a phase transfer catalyst at a temperature in the range of about 30° to 150° C., preferably about 40° to about 100° C., and most preferably about 50° to about 70° C. The reaction may be carried out in the presence of a solvent such as a hydrocarbon, an ether, or a ketone, but use of an excess of epichlorohydrin as the solvent is preferred.

Suitable alkali include sodium hydroxide, potassium hydroxide and calcium hydroxide. Sodium hydroxide is preferred.

Suitable phase transfer catalysts include tetraalkylammonium halides such as methyltrioctylammonium chloride, methyltridecylammonium chloride or tetramethylammonium chloride or a tertiary amine or quaternary ammonium base such as benzyltrimethylammonium or a quaternary ammonium salt such as benzyltrimethylammonium chloride. Benzyltrimethylammonium chloride and tetramethylammonium chloride are preferred. The phase transfer catalyst is generally used in an amount of about 0.1 to about 5 wt %, preferably about 0.5 to about 2 wt % and most preferably about 0.8 to about 1.2 wt % based upon the total weight of the reactants.

Preferably, water is removed continuously as an azeotrope with epichlorohydrin. The diglycidyl ether reaction product can be washed with water to remove the sodium chloride formed and the excess epichlorohydrin can optionally be removed by distillation.

The resulting diglycidyl ether with a monomer content of about 60 to about 75% is then further reacted with epichlorohydrin in the presence of an alkali and benzyltrimethylammonium chloride to produce a glycidyl ether with a monomer content of about 80 to about 90%.

Preferably, the diglycidyl ether is reacted with at least about 0.2, and preferably about 3 to about 8 molar equivalents of epichlorohydrin in the presence of about 0.1 to about 2.0 moles, preferably about 0.5 to about 1.5 moles, most preferably 1.0 moles of an alkali and in the presence of about 0.1 to about 1.0 wt % of benzyltrimethylammonium chloride based on the total weight of the reactants at a temperature in the range of about 30° to 150° C., preferably about 40° to about 100° C., and most preferably about 50° to about 70° C. The reaction may be carried out in the presence of a solvent such as a hydrocarbon, an ether, or a ketone, but use of an excess of epichlorohydrin as the solvent is preferred.

Suitable alkali include sodium hydroxide, potassium hydroxide and calcium hydroxide. Sodium hydroxide is preferred.

The benzyltrimethylammonium chloride is preferably used in an amount of about 0.1 to about 1.0 wt % and most preferably about 0.3 to about 0.5 wt % based upon the total weight of the reactants.

Preferably, water is removed continuously as an azeotrope with epichlorohydrin. The diglycidyl ether reaction product can be washed with water to remove the sodium chloride formed and the excess epichlorohydrin can be removed by distillation.

Particularly preferred diglycidyl ethers of di-secondary alcohols which are prepared by the processes of the present invention include the following specific examples:

2,2-bis(p-(3-butoxy-2-glycidyloxypropyloxy)phenyl)-propane;
2,2-bis(p-(3-methoxy-2-glycidyloxypropyloxy)phenyl)-propane;
2,2-bis(p-(3-ethoxy-2-glycidyloxypropyloxy)phenyl)-propane;
2,2-bis(p-(3-dodecyloxy-2-glycidyloxypropyloxy)-phenyl)-propane;

2,2-bis(p-(3-tetradecyloxy-2-glycidyloxypropyloxy)-phenyl)-propane;
2,2-bis(p-(3-benzyloxy-2-glycidyloxypropyloxy)-phenyl)propane;
bis(p-(3-butoxy-2-glycidyloxypropyloxy)phenyl)methane;
1,3-bis(3-phenoxy-2-glycidyloxypropyloxy)benzene;
bis(p-(3-butoxy-2-glycidyloxypropyloxy)phenyl)sulphone;
2,2-bis(p-(3-cyclohexyloxy-2-glycidyloxypropyloxy)-phenyl)propane;
2,2-bis(4-(3-butoxy-2-glycidyloxypropyloxy)-3,5-dibromophenyl)propane;
2,2-bis(p-(3-allyloxy-2-glycidyloxypropyloxy)phenyl)-propane;
2,2-bis(p-(3-benzyloxy-2-glycidyloxypropyloxy)-phenyl)propane;
1,3-bis(2-glycidyloxy-3-phenoxypropyloxy)benzene; and
2,2-bis(p-(3-phenoxy-2-glycidyloxypropyloxy)phenyl)-propane.

The glycidyl ethers of the formula I are curable resins and are particularly suitable for use in castings. Suitable methods and compositions in which the glycidyl ethers of formula I find utility are known in the art as set forth in U.S. Pat. No. 4,284,574, which is hereby incorporated by reference.

The following examples serve to give specific illustrations of the practice of this invention but they are not intended in any way to limit the scope of this invention.

EXAMPLE 1

This example illustrates the preparation of a typical glycidyl ether of the present invention using a two step process.

Step (a) 2,2-Bis(p-(3-butoxy-2-hydroxypropyloxy)-phenyl)-propane (244 g; 1.0 equiv.), epichlorohydrin (740 g; 8 moles), and 50% aqueous tetramethylammonium chloride (6.6 g) are stirred and heated under a partial vacuum to maintain a gentle reflux at 50°-60° C. A 50% aqueous sodium hydroxide solution (84 g; 1.05 mole) is added dropwise over 3 hours, water being removed continuously as an azeotrope with epichlorohydrin. The mixture is cooled, and washed repeatedly with water to remove the sodium chloride formed. The excess of epichlorohydrin is removed by distillation under reduced pressure to leave 2,2-bis(p-(3-butoxy-2-glycidyloxypropyloxyphenyl)propane (283 g), which had an epoxide content of 2.86 equiv./kg (theoretical value 3.32 equiv./kg). Monomer content of 70% (HPLC). Its viscosity at 25° C. to 1050 cps.

Step (b) 2,2-Bis(p-(3-butoxy-2-glycidylpropyloxy)-phenyl)-propane (610 g; 2 equiv.), epichlorohydrin (1200 g; 13 equiv.) and 50% aqueous benzyltrimethylammonium chloride (12 g) are stirred and heated under a partial vacuum to maintain a gentle reflux at 50°-60° C. A 50% aqueous sodium hydroxide solution (90 g; 1.1 equiv.) is added dropwise over 3 hours, water being removed continuously as an azeotrope with epichlorohydrin. The mixture is cooled, neutralized to a pH of 6-7 and washed repeatedly with water to remove the salt formed. The excess of epichlorohydrin is removed by distillation under reduced pressure to leave 2,2-Bis(p-(3-butoxy-2-glycidyloxypropyloxy)phenyl)-propane (600 g) which has an epoxide content of 3.30 equivalent/kg, monomer content of 86.5%. Its viscosity at 25° C. is 1020 cps.

EXAMPLE 2

This example illustrates the preparation of a typical glycidyl ether of the present invention using a continuous process.

2,2-Bis(p-(3-butoxy-2-hydroxypropyloxy)phenyl)-propane (244 g; 1.0 equiv.), epichlorohydrin (740 g; 8 moles) and 50% aqueous benzyltrimethylammonium chloride (7.0 g) are stirred and heated under a partial vacuum to maintain a gentle reflux at 50°-60° C. A 50% aqueous sodium hydroxide solution (84 g; 1.05 mole) is added dropwise over 3 hours, water being removed continuously as an azeotrope with epichlorohydrin. The mixture is cooled and washed twice with 300 ml of water to remove salt formed. To the organic solution is added 50% aqueous benzyltrimethylammonium chloride (2.8 g) and the reaction mixture is stirred and heated under a partial vacuum to maintain a gentle reflux at 50°-60° C. A 50% aqueous sodium hydroxide solution (43 g; 0.53 equiv.) is added dropwise over 3 hours, water being removed continuously as an azeotrope with epichlorohydrin. The mixture is cooled, neutralized to a pH of 6-7 and washed repeatedly with water to remove the salt formed. The excess of epichlorohydrin is removed by distillation under reduced pressure to leave 2,2-Bis(p-(3-butoxy-2-glycidyloxypropyloxy)phenyl)propane (280 g) which has an epoxide content of 3.30 equivalent/kg and a monomer content of 85.5% (HPLC). Its viscosity at 25° C. is 1017 cps.

What is claimed is:

1. A process for the preparation of a glycidyl ether of a di-secondary alcohol with a monomer content of about 80% to about 90% of the formula (I)

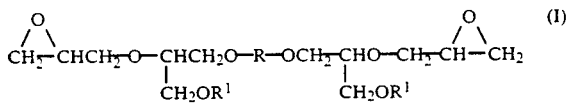

where R represents
(i) a phenylene or naphthylene group or
(ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms, each phenylene group or each naphthylene group optionally being substituted in the ring or rings by one or two alkyl groups, each of from 1 to 4 carbon atoms, or by one or two chlorine or bromine atoms, and each $R^1$ represents (iii) a straight chain or branched alkyl groups of 1 to 16 carbon atoms, which may be substituted by one to four chlorine or bromine atoms, or
(iv) a straight chain or branched alkenyl group of 2 to 6 carbon atoms, which may be substituted by one to four chlorine or bromine atoms, or
(v) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or
(vi) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or (vii) a mononuclear cycloalkyl group of 3 to 6 carbon atoms, or (viii) a mononuclear cycloalkylalkyl group of from 4 to 10 carbon atoms comprising the steps of:

(a) reacting a di-secondary alcohol of the formula (II)

$$H-O-CHCH_2O-R-OCH_2-CHO-H \quad (II)$$
$$\phantom{H-O-C}CH_2OR^1 \phantom{-R-OCH_2-}CH_2OR^1$$

wherein R and $R^1$ are defined hereinabove, with epichlorohydrin in the presence of an alkali and a phase transfer catalyst to produce a glycidyl ether with a monomer content of about 60% to about 75%; and (b) reacting said glycidyl ether with a monomer content of about 60% to about 75% with epichlorohydrin in the presence of an alkali and benzyltrimethylammonium chloride to produce a glycidyl ether of a di-secondary alcohol with a monomer content of about 80% to about 90%.

2. A process according to claim 1 wherein the groups $R^1$ are the same and each represents an alkyl group of 1 to 14 carbon atoms, an allyl group, a cyclohexyl group, or a benzyl group.

3. A process according to claim 1 wherein $R^1$ is an alkyl group of 1 to 14 carbon atoms.

4. A process according to claim 1 wherein R is a m- or p-phenylene group or a radical consisting of two phenylene rings linked in the o-o', o-p', or p-p' position by an alkylene group of 1 to 4 carbon atoms.

5. A process according to claim 1 wherein R represents a group of the formula

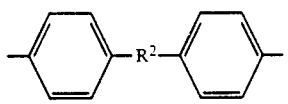

where $R^2$ represents a methylene or isopropylidene group, and each $R^1$ represents an alkyl group of from 1 to 12 carbon atoms.

6. A process according to claim 1 wherein R represents a group of the formula

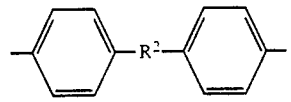

where $R^2$ represents a methylene or isopropylidene group, and each $R^1$ represents an alkyl group of from 1 to 6 carbon atoms.

7. A process according to claim 1 wherein said di-secondary alcohol is reacted with at least about 2.5 molar equivalents of epichlorohydrin.

8. A process according to claim 1 wherein said di-secondary alcohol is reacted with about 3 to 8 molar equivalents of epichlorohydrin.

9. A process according to claim 1 wherein the reaction of the di-secondary alcohol is carried out in the presence of about 2.0 to about 2.5 moles of an alkali.

10. A process according to claim 1 wherein step (a) is carried out at a temperature in the range of about 30° to 150° C.

11. A process according to claim 9 wherein said alkali is sodium hydroxide.

12. A process according to claim 1 wherein the phase catalyst in step (a) is selected from the group consisting of methyltrioctylammonium chloride, methyltridecylammonium chloride, tetramethylammonium chloride, and benzyltrimethylammonium chloride.

13. A process according to claim 1 wherein said phase transfer catalyst is present in an amount of about 0.1 to about 1 wt % based upon the total weight of the reactants.

14. A process according to claim 1 wherein said diglycidyl ether is reacted with at least about 0.2 molar equivalents of epichlorohydrin.

15. A process according to claim 1 wherein said diglycidyl ether is reacted with about 3 to about 8 molar equivalents of epichlorohydrin.

16. A process according to claim 1 wherein the reaction of the diglycidyl ether is carried out in the presence of about 1.5 to about 2.5 moles of an alkali.

17. A process according to claim 1 wherein step (b) is carried out at a temperature in the range of about 30° to 150° C.

18. A process according to claim 16 wherein said alkali is sodium hydroxide.

19. A process according to claim 1 wherein step (b) is carried out in the presence of about 0.1 to about 1.0 wt % of benzyltrimethylammonium chloride based on the total weight of the reactants.

20. A process according to claim 1 wherein step (b) is carried out in the presence of about 0.3 to about 0.5 wt % of benzyltrimethylammonium chloride based on the total weight of the reactants.

* * * * *